US012053235B2

(12) United States Patent
Sreekar et al.

(10) Patent No.: US 12,053,235 B2
(45) Date of Patent: Aug. 6, 2024

(54) SYSTEM AND METHOD FOR THE ABLATION OF UTERINE FIBROIDS

(71) Applicant: NESA MEDTECH, Karnataka (IN)

(72) Inventors: Kothamachu Sreekar, Bangalore (IN); B. R. Usha, Bangalore (IN); Bai P. Lakshmi, Bangalore (IN); Abraham Philip Anish, Thiruvananthapuram (IN); Jose P. Arun, Thrissur (IN); Patil Vikram, Mysuru (IN); Pradhan Debasish, Sambalpur (IN)

(73) Assignee: NESA MEDTECH, Karnataka (IN)

( * ) Notice: Subject to any disclaimer, the term of this patent is extended or adjusted under 35 U.S.C. 154(b) by 678 days.

(21) Appl. No.: 17/271,038

(22) PCT Filed: Aug. 27, 2019

(86) PCT No.: PCT/IB2019/057199
§ 371 (c)(1),
(2) Date: Feb. 24, 2021

(87) PCT Pub. No.: WO2020/044227
PCT Pub. Date: Mar. 5, 2020

(65) Prior Publication Data
US 2021/0322092 A1    Oct. 21, 2021

(30) Foreign Application Priority Data

Aug. 27, 2018    (IN) .............................. 201841028351

(51) Int. Cl.
*A61B 8/08* (2006.01)
*A61B 8/00* (2006.01)
(Continued)

(52) U.S. Cl.
CPC .......... *A61B 18/1485* (2013.01); *A61B 8/085* (2013.01); *A61B 8/12* (2013.01);
(Continued)

(58) Field of Classification Search
CPC ....... A61B 18/1485; A61B 8/085; A61B 8/12; A61B 8/466; A61B 8/483; A61B 18/02;
(Continued)

(56) References Cited

U.S. PATENT DOCUMENTS 6,231,591 B1 * 5/2001 Desai ............... A61B 17/00234
604/8
2017/0290626 A1    10/2017 Deckman et al.

FOREIGN PATENT DOCUMENTS

WO    WO-2018089523 A1 *    5/2018    ......... A61B 18/1477

* cited by examiner

*Primary Examiner* — Rochelle D Turchen
(74) *Attorney, Agent, or Firm* — Harness, Dickey & Pierce, P.L.C.

(57) ABSTRACT

The present disclosure provides a system for ablation of uterine fibroid(s), said system comprising: an ultrasound scanner configured to perform a volume scan of a uterus of a patient; a display coupled with the ultrasound scanner, configured for displaying image and alphanumeric characters; a device comprising an electrode for ablating the uterine fibroid; a controllable energy source coupled with the electrode and configured to supply energy to the electrode. The system comprises one or more processors configured to: receive ultrasound image data from the ultrasound scanner; process the image data to generate a three-dimensional representation of the uterus of the patient; determine location and size of one or more fibroids in the uterus; determine one or more navigation parameters for the electrode, from the display; determine ablation parameters required by the electrode to ablate the fibroid, wherein the device is operatively coupled to the one or more processors, said one or more processors configured to guide the electrode to a required point in the fibroid based on the determined one or more navigation parameters on the display, and wherein, on receipt of a signal, the controllable energy source supplies power to electrode to enable ablation of the fibroid.

27 Claims, 6 Drawing Sheets

(51) Int. Cl.
*A61B 8/12* (2006.01)
*A61B 18/02* (2006.01)
*A61B 18/14* (2006.01)
*A61B 18/18* (2006.01)
*A61B 18/20* (2006.01)
*A61B 34/20* (2016.01)
*A61B 18/00* (2006.01)

(52) U.S. Cl.
CPC .............. *A61B 8/466* (2013.01); *A61B 8/483* (2013.01); *A61B 18/02* (2013.01); *A61B 18/1815* (2013.01); *A61B 18/20* (2013.01); *A61B 34/20* (2016.02); A61B 2018/00559 (2013.01); A61B 2018/00577 (2013.01); A61B 2018/00702 (2013.01); A61B 2018/0212 (2013.01); A61B 2018/1475 (2013.01); A61B 2034/2063 (2016.02)

(58) Field of Classification Search
CPC ..... A61B 18/1815; A61B 18/20; A61B 34/20; A61B 2018/00559; A61B 2018/00577; A61B 2018/00702; A61B 2018/0212; A61B 2018/1475; A61B 2034/2063; A61B 8/463; A61B 2034/107; A61B 2017/00455; A61B 2034/2065; A61B 2090/3784; A61B 34/10; A61B 2017/4216; A61B 2034/105; A61B 2090/061; A61B 2090/067; A61B 2090/0807

See application file for complete search history.

SYSTEM AND METHOD FOR THE ABLATION OF UTERINE FIBROIDS

CROSS-REFERENCE TO RELATED APPLICATIONS

This application is a U.S. National Phase Application under 35 U.S.C. 371 of International Application No. PCT/IB2019/057199, filed on Aug. 27, 2019, which claims the benefit of Indian Patent Application No. 201841028351, filed on Aug. 27, 2018. The disclosure of each of the above-identified applications is incorporated herein by reference.

TECHNICAL FIELD

The present disclosure relates generally to an approach for ablation of uterine fibroids. In particular, the present disclosure relates to an approach for safe ablation of uterine fibroids using real-time guidance and monitoring.

BACKGROUND

One of the most common gynaecological problems is fibroids in the uterus, commonly called uterine fibroids. While in many women, the fibroids are asymptomatic and even may go undetected. In others, it is symptomatic and may need treatment.

The first line of treatment is management of symptoms using medication. This however is temporary and eventually most women with symptomatic uterine fibroids are advised surgery.

The most common surgery is hysterectomy, that is, the removal of the uterus. This suffers from high morbidity, long recovery time, and a possibility of damage to organs close to the uterus and other known undesirable side effects. This is also a solution that requires skilled surgical gynaecologist's intervention and is performed under general anaesthesia. Hospitalization has an economical as well as social burden and a considerable loss of working days for the patient and the family.

The second surgical option is the removal of fibroids through surgery. It is also possible that the surgery is either performed through laparotomy or laparoscopically. This needs highly skilled surgeons to perform the surgery and it is performed under general anaesthesia. This also makes the procedure expensive compounded by the fact that there are too few such skilled surgical gynaecologists to meet the demand, especially in rural or remote areas. This makes such surgical procedures out of reach and unaffordable for a large percent of the population. In spite of all these the success rate is not as high as desired.

The third method is Magnetic Resonance guided Focused Ultrasound (normally referred to as MRgFUS in the field). While this has some distinct advantages such as being a non-invasive procedure, suffers from the disadvantage that it requires a very expensive MRI scanner and specialized ultrasound equipment. It is also performed by highly skilled and trained interventional radiologists. Such radiologists are also very few to meet the demand, even if cost is not a factor.

The fourth alternative is uterine artery embolization. In this procedure, the arteries supplying blood to the fibroids are identified in a catheterization laboratory commonly referred to as a Cath Lab. A catheter is guided into these arteries and sealed with a sealant such that blood supply to the fibroids are cut off. This leads to necrosis of the fibroids which are then shed by the uterus or absorbed by the surrounding tissue. The disadvantages of this procedure are the need of a highly expensive infrastructure namely the Cath Lab, the fact that they are applicable only for a limited set of or types of fibroids, it is traumatic for the patient, to name a few.

The fifth alternative uses radio frequency ablation or RF ablation in short. It is carried out by accessing a fibroid with an electrode, passing radio frequency energy through the electrode and ablating the fibroid. This is carried out under the guidance of ultrasound imaging. The electrode is inserted to reach the fibroid to be ablated either through the abdomen of the patient or through the cervix. In both the cases needs piercing of the tissue. This is a minimally invasive method and hence devoid of some of the disadvantages of surgery. However, this procedure also requires highly skilled and trained gynaecologists and requires the use of an operating theatre. This procedure suffers from incomplete removal of fibroids, frequent recurrence of the fibroids and also often causes damage to the organs situated close to the uterus because of the limitations of performing the procedure with the existing ultrasound machine and only the RF electrode. However, this has not found widespread application and is practiced only in a few advanced countries, such as South Korea, Denmark, Italy, for instance.

In view of the aforementioned disadvantages, there is a need for a system that can overcome said disadvantages, a system for ablation of fibroids that comprises a system able to integrate with an ultrasound machine preferably those normally available with a gynaecologist and preferably does not require specialized skills to operate the same. Further, there is an unmet need for a method for ablation of fibroids that is minimally invasive, that can be carried out in a limited resource setting even outside of an operating theatre by a gynaecologist, with a reasonable amount of training.

SUMMARY

The present disclosure relates generally to an approach for ablation of uterine fibroids. In particular, the present disclosure relates to an approach for safe ablation using real-time guidance and monitoring.

In an aspect, the present disclosure provides a system for ablation of uterine fibroid(s), said system comprising: an ultrasound scanner configured to perform a volume scan of a uterus of a patient; a display coupled with the ultrasound scanner, configured for displaying image and alphanumeric characters; a device comprising an electrode for ablating the uterine fibroid; a controllable energy source coupled with the electrode and configured to supply energy to the electrode; one or more processors operatively coupled with a memory, said memory storing instructions executable by the one or more processors to: receive ultrasound image data from the ultrasound scanner; process the image data to generate a three-dimensional representation of the uterus of the patient; determine location and size of one or more fibroids in the uterus; determine one or more navigation parameters for the electrode, from the display; determine ablation parameters required by the electrode to ablate the fibroid, wherein the device is operatively coupled to the one or more processors, said one or more processors configured to guide the electrode to a required point in the fibroid based on the determined one or more navigation parameters on the display, and wherein, on receipt of a signal, the controllable energy source supplies power to electrode to enable ablation of the fibroid.

In an embodiment, the transducer is introduced through the vagina of a patient for carrying out a trans-vaginal scan of the uterus.

In another embodiment, the device is introduced through the vagina of a patient and is further guided into the uterus through the cervix.

In another embodiment, the controllable energy source is selected from a group comprising RF source, microwave source, laser source and cryo source.

In another embodiment, the energy source includes control means to set the ablation parameters for the ablation of the fibroid, and to set the duration of the ablation process.

In another embodiment, the processing of the ultrasound images occurs on a planning workstation.

In another embodiment, the device for carrying out ablation of uterine fibroid(s) comprises: a sheath provided at an end of the device, said end being in a direction of insertion of the device into the uterine cavity, said sheath covering an electrode provided on the device that is configured for ablation of uterine fibroid(s); an angle provided towards a distal end of the sheath, wherein the angle enables the end of the sheath to reach the one or more fibroids in the uterus; markings provided on the sheath to enable determination of extent of insertion of the device into the uterine cavity; rotary markings provided on the device to enable determination of rotational orientation of the sheath; and a rotary mechanism provided in the carriage barrel assembly such that rotation applied to the mechanism causes a linear motion of the electrode outwards from the sheath to enable the electrode to pierce the uterine fibroid(s).

In another embodiment, the planning workstation is configured to, based on the processed image data, compute navigational parameters selected from a group comprising the length of insertion of the sheath in order that the sheath is positioned close to the fibroid, orientation of the device required such that the sheath is positioned with respect to a required point in the fibroid, the length of electrode required to be pushed from the sheath to reach the required point in the fibroid and a combination thereof.

In another embodiment, the planning workstation, based on the processed image data, is configured to determine the ablation parameters from the location and size of the fibroid from a database operatively coupled to the planning workstation, said database containing a dataset of corresponding parameters for ablation of a plurality of fibroids.

In another embodiment, based on the ablation parameters of a selected uterine fibroid, a safe volume for ablation of the fibroid is computed and represented graphically, based on presence of tissues in the vicinity of the fibroid that are not meant to be ablated.

In another embodiment, the planning workstation provides real time guidance and tracking while the electrode is being positioned at the required point in the fibroid.

In an aspect, the present disclosure provides a device for carrying out ablation of uterine fibroid(s), said device comprising: a sheath provided at an end of the device, said end being in a direction of insertion of the device into the uterine cavity, said sheath covering an electrode provided on the device that is configured for ablation of uterine fibroid(s); an angle provided towards a distal end of the sheath, wherein the angle enables the end of the sheath to reach walls of the uterine cavity, and wherein the angle affords support to the electrode; markings provided on the sheath to enable determination of extent of insertion of the device into the uterine cavity; rotary markings provided on the device to enable determination of rotational orientation of the sheath; and a rotary mechanism provided in the carriage barrel assembly such that rotation applied to the mechanism causes a linear motion of the electrode outwards from the sheath to enable the electrode to pierce the uterine fibroid(s).

In an embodiment, the angle provided is not more than 24 degrees and is in the range of 15 degrees to 24 degrees. In an exemplary embodiment, the angle provided is 15 degrees.

In another embodiment, the rotary mechanism enables generation of force not less than 20 N, and in the range of 20 N and 38 N to enable the electrode to pierce the uterine fibroid(s).

In another embodiment, the device is provided with sheath markings on the sheath to determine extent of insertion of the sheath into the uterus, the sheath markings preferably being separated by 5 mm.

In another embodiment, the device is provided with electrode markings to determine extent of extension of the electrode, the electrode markings preferably being separated by 2.5 mm.

In another embodiment, the device is provided with orientation markings to enable determination of the orientation of the angle of the sheath within the uterine cavity.

In another embodiment, the device is provided with an actuator configured to initiate outward extension of the electrode.

In another embodiment, the device is configured to be operated by any or a combination of manual means, electronic means and a combination thereof based on navigation parameters displayed on a visual display operatively coupled to the device, to enable the device to be guided to a required point for ablation of the uterine fibroid.

In another embodiment, the device is coupled to an energy source such that, on receipt of an instruction, the energy source is configured to provide ablation parameters and energy to the electrode to enable ablation of the fibroid(s).

In an aspect, the present disclosure provides a method for ablation of uterine fibroid(s), the method comprising the steps of: performing, using an ultrasound scanner, a volume scan of a uterus of a patient; receiving, at a computing device, ultrasound image data from the ultrasound scanner, said ultrasound image data being displayed on a display configured for image and alphanumeric characters; processing, at the computing device, the ultrasound image data to generate a three-dimensional representation of the uterus of the patient; determining, at the computing device, location and size of one or more fibroids in the uterus; determining, at the computing device, one or more navigation parameters for guiding a device at a required point in the fibroid in the uterus; determining, at the computing device, ablation parameters required by the electrode to ablate the fibroid; guiding, using one or more navigation parameters computed by a computing device, the device to enable the electrode to be positioned at the required point in the fibroid, wherein, on receipt of a signal, the controllable energy source supplies power to electrode to enable ablation of the fibroid.

In an embodiment, the transducer is introduced through the vagina of a patient for carrying out a trans-vaginal scan of the uterus.

In another embodiment, the device is introduced through the vagina of a patient and is further guided into the uterus through the cervix.

In another embodiment, the controllable energy source is selected from a group comprising RF source, microwave source, laser source and cryo source.

In another embodiment, the energy source includes control means to set the ablation parameters for the ablation of the fibroid, and to set the duration of the ablation process.

In another embodiment, the processing of the ultrasound images occurs on a planning workstation.

In another embodiment, the planning workstation is configured to, based on the processed image data, compute navigational parameters selected from a group comprising the length of insertion of the sheath in order that the sheath is positioned close to the fibroid, orientation of the device required such that the sheath is positioned with respect to a required point in the fibroid, the length of electrode required to be pushed from the sheath to reach the required point in the fibroid and a combination thereof.

In another embodiment, the planning workstation, based on the processed image data, is configured to determine the ablation parameters from the location and size of the fibroid from a database operatively coupled to the planning workstation, said database containing a dataset of corresponding parameters for ablation of a plurality of fibroids.

In another embodiment, based on the ablation parameters of a selected uterine fibroid, a safe volume for ablation of the fibroid is computed and represented graphically, based on presence of tissues in the vicinity of the fibroid that are not meant to be ablated.

In another embodiment, the planning workstation provides real time guidance and tracking while the electrode is being positioned at the required point in the fibroid.

Various terms are used herein. To the extent a term used in a claim is not defined below, it should be given the broadest definition persons in the pertinent art have given that term as reflected in printed publications and issued patents at the time of filing.

BRIEF DESCRIPTION OF THE DRAWINGS

The following drawings form part of the present specification and are included to further illustrate aspects of the present disclosure. The disclosure may be better understood by reference to the drawings in combination with the detailed description of the specific embodiments presented herein.

DETAILED DESCRIPTION

Figure 1:
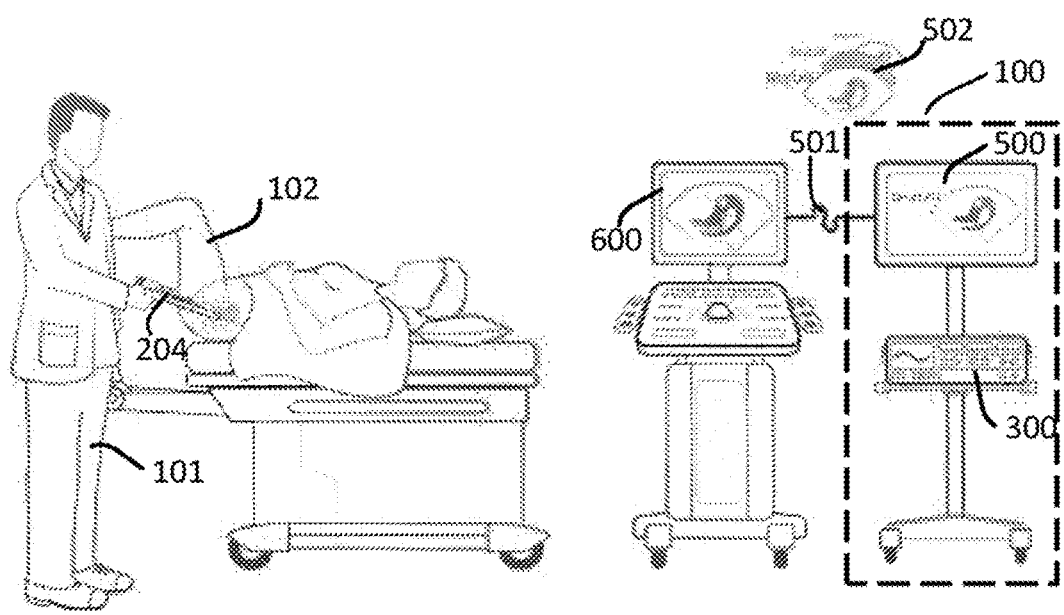
FIG. 1 illustrates an exemplary system for ablation of uterine fibroids, as per one of the embodiments of the present disclosure.

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

The expression "Minor Operation Theatre" and "Minor OT" is used throughout to refer to a place of work of a gynaecologist.

The terms "RF generator" or "RF source" or "source of RF power" are used interchangeably and means a source capable of generating and providing radio frequency power.

The expression "radio frequency electrode' is interchangeably referred as "RF electrode" or "RF ablation needle", among other expressions which would generally be known to a person skilled in the art.

The expressions "input provider" as used herein mean a "gynaecologist" or a "surgeon" or a "doctor" or a "medical professional" or a trained person capable of providing instructions to planning workstation and/or any component of the system.

The present disclosure describes a system using RF power for enabling ablation of uterine fibroid(s). However, it can be appreciated by persons skilled in the art that the electrode can be provided with other sources of power such as laser, microwave, cryo source etc. The use of RF power is intended as an illustration of the present system and may not be construed as a limitation.

The present disclosure, in a general aspect, provides a system for ablation of uterine fibroid(s). The system can have one or more characteristics of being a minimally invasive, cost effective, safe and clinically effective system to treat uterine fibroids. Further it is preferable that such a system does not need a highly skilled gynaecologist to operate said system. Still further, the system can be operated outside of an operating theatre to treat uterine fibroids. In other words, the system can be operated in a limited resource setting of the gynaecologist's office commonly referred to as a minor operation theatre or in-office. The system, in accordance with an embodiment of the present disclosure, can be integrated with ultrasound machine and energy sources of any make that are normally available to a gynaecologist, thereby rendering the system versatile and cost effective.

In one aspect, the present disclosure provides a system for ablation of uterine fibroid(s), the system comprising:
a) an ultrasound scanner functionally and detachably connected to a planning workstation;
b) an ultrasound transducer functionally coupled to the ultrasound scanner; and
c) a device for ablation, provided with an RF electrode and being operably coupled to a central computing device (hereinafter, also referred to as planning workstation) and connected at the end other than the end to enter the uterus, to a controllable source of RF power to deliver power to the RF electrode for ablation of the fibroid.

The ultrasound scanner is the one that is known and used by a person skilled in the art, for example, the ultrasound scanner usually found in the surgeon or gynaecologist's clinic or office.

The energy source for the electrode can be any as known in the art.

The ultrasound transducer, which is functionally coupled to the ultrasound scanner is used for a trans-vaginal volume scan. The transducer is capable of being introduced through the vagina of a patient for carrying out trans-vaginal volume scan of the uterus, as generally performed currently.

In an embodiment, the RF electrode comprises a tubular structure with a diameter of approximately 1 mm. The electrode is provided with a protective, sheath on the outside of the electrode. The device can be provided with a means that enables the surgeon/gynaecologist to push the electrode out through the sheath to expose a required length (or active length) of the distal end of the RF electrode. Here, the required length can be defined as the length of electrode required to be pushed from the device so as to enable the electrode to reach the fibroid and pierce it. The active length of the electrode can be defined as the length of the electrode that is required to transfer RF energy to the fibroid for the ablation of the fibroid. Typically, the active length of the electrode is smaller than the required length of the electrode. The use of only the active length of the electrode for the purpose of ablation improves the aspect of safety of the in that, the electrode does not, inadvertently, cause damage to healthy tissue.

In an embodiment, a part of the device carrying the electrode can be introduced through the vagina of a patient and can be further guided into the uterus through the cervix by a skilled person such as a doctor or other medical professionals. The device is manoeuvred based on navigation parameters provided by the planning workstation, to enable the RF electrode to enter the uterus and be being positioned to any point within the uterus. The navigation parameters as mentioned above can include, but not be limited to length of insertion of the sheath in order that the sheath is positioned close to the fibroid, orientation of the device required such that the sheath is positioned with respect to a required point in the fibroid and the length of electrode required to be pushed from the sheath to reach the required point in the fibroid.

The device is preferably capable of being controlled by manual controls provided therewith. The manual controls can also include a means to enable retraction of a sheath component of the RF electrode to expose a required length of the distal end of the RF electrode.

In an embodiment the RF source is operably connected to a means to provide a command to the RF source to deliver the RF power to the RF electrode for initiating the ablation of the uterine fibroid. The means to provide the command can be for example a push button or a foot pedal operably connected to the RF source.

In an embodiment the RF source includes control means to set the ablation parameters for necrosis of the fibroid, and to set the duration of the ablation process.

In an embodiment, the planning workstation can be a digital computer that is functionally and detachably connected to the ultrasound scanner 600. The computer is preferably what is known as a desktop, in the field of computers. The computer is of specifications, at least sufficient to carry out the desired tasks. The computer is pre-loaded with the dedicated software according the disclosed method.

In an embodiment, the computer can be preloaded with the dedicated software to enable the computer to receive images obtained by the ultrasound machine and store them for further processing. Accordingly, the digital computer is referred to in the further description is the planning workstation. The planning workstation is capable of providing the real time or near real time images of the RF electrode in the uterus. The visual guidance may be in the form of an overlaid guiding line on the displayed ultrasound image, the overlay being an inventive feature of the software of the system of the present disclosure.

The planning workstation also provides the ablation parameters for each of the fibroids. The ablation parameters may be one or more of a power and duration of the ablation. The planning workstation is also configured to recommend the positioning of the exposed length of the RF electrode.

The system is further configured to provide a graphical representation of ablation volume of a fibroid to be ablated. When any of the one or more uterine fibroids is be selected, the volume of ablation of the fibroid in the uterus is computed and graphically represented. The computation occurs based on the ablation parameters and the presence of non-fibroid tissue that is not meant to be ablated. In an exemplary embodiment, the ablation region is about 5 to 10 mm from any of the non-fibroid tissues present that are not meant to be ablated.

The planning workstation, based on the images provided by the ultrasound scanner is also configured to provide recommendations of the sequence in which the fibroids are to be ablated in case there are more than one fibroid. The sequence is based on the relative distance of a fibroid from the point of insertion of the device into the uterus. The fibroid farthest from the point of insertion is first ablated, and the remaining fibroids are ablated based on a decreasing distance from the point of insertion of the device. In other words, the fibroids are ablated from the farthest to the nearest, with respect to the point of insertion of the device into the uterus.

FIG. 1 illustrates an exemplary system for ablation of uterine fibroids, as per one of the embodiments of the present disclosure. The system comprises an ultrasound scanner 600 functionally coupled to an ultrasound transducer 202 for taking trans-vaginal scan. The ultrasound transducer 202 can further be coupled with the planning workstation. The ultrasound transducer 202 is adapted to be introduced through the vagina of a patient and is further adapted to perform a trans-vaginal scan of the uterus of the patient. In the disclosed system, the device 204 is adapted to be introduced through the vagina of a patient to reach the uterus, being guided through the cervix of the patient. The device 204 can be guided to manoeuvre through the uterus to be positioned at an area or point of interest on the uterus. The guidance can be manually controlled by a medical professional, based on navigational parameters provided by the planning workstation. The device 204 is adapted to enter the uterus at an end of the device 204, which comprises an electrode 200. The electrode is coupled with a controllable source of power 300 such as RF, microwave, laser source, cryo source etc. such that when power is delivered to the electrode, the electrode can perform an ablation procedure on the uterine fibroid(s). the power source 300 can be configured with means to control power output of the power. A signal to operate the power source 300 can come from a switch such as a foot pedal.

In another embodiment, an ultrasound scanner 600, which can receive the ultrasound images from the transducer 202 can be operatively coupled with the planning workstation 500, which is configured to receive ultrasound images and process them.

Figure 2:
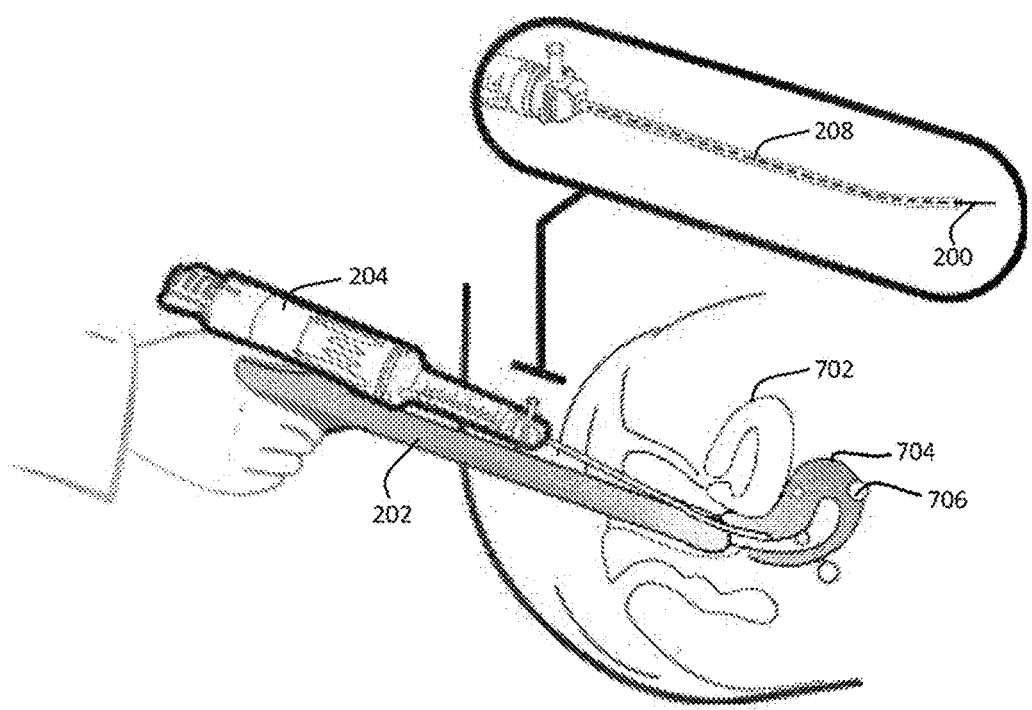
FIG. 2 illustrates a representation of the working of the ultrasound transducer and the device for ablation of uterine fibroids, in accordance with an embodiment of the present disclosure.

FIG. 2 illustrates a representation of the working of the ultrasound transducer and the device for ablation of uterine fibroids, in accordance with an embodiment of the present disclosure. The device 204 consists of a minimally invasive probe and a sheath 208. The electrode 200 is provided within the sheath 208, which can be exposed when the electrode 200 is pushed out of the sheath 208. The device can be coupled to a control means to enable the surgeon/gynaecologist to push the electrode out through the sheath to expose a required length of the electrode 200 when the sheath is positioned near the required area of the uterus having the uterine fibroid(s).

Having introduced the different elements of the inventive system, a brief description of operation of the system to carry out the ablation of uterine fibroid(s) will be now be described. It is to be noted that the disclosure is not concerned with the treatment of fibroids but is concerned with the system to carry out the ablation of uterine fibroid(s) for the treatment. The procedure is described here only to illustrate the operation and function of the elements of the system and how the system works as a whole.

In some embodiments, the patient is anesthetized with a local anaesthetic. This ensures that the patient does not feel the pain and discomfort associated with the procedure. The ultrasound transducer 202 is inserted through the vagina so that the distal end of the transducer reaches the cervix. For the sake clarity, it is noted that the proximal end of the transducer has the cables for connecting to the ultrasound scanner 600 and is handled by the gynaecologist to position the transducer 202 on the cervix. The distal end of the transducer is then swept along the cervix to acquire a volume scan of entire uterus in different orientations. The resultant images from the ultrasound scanner 600, are recorded at the planning workstation 500.

Figure 3:
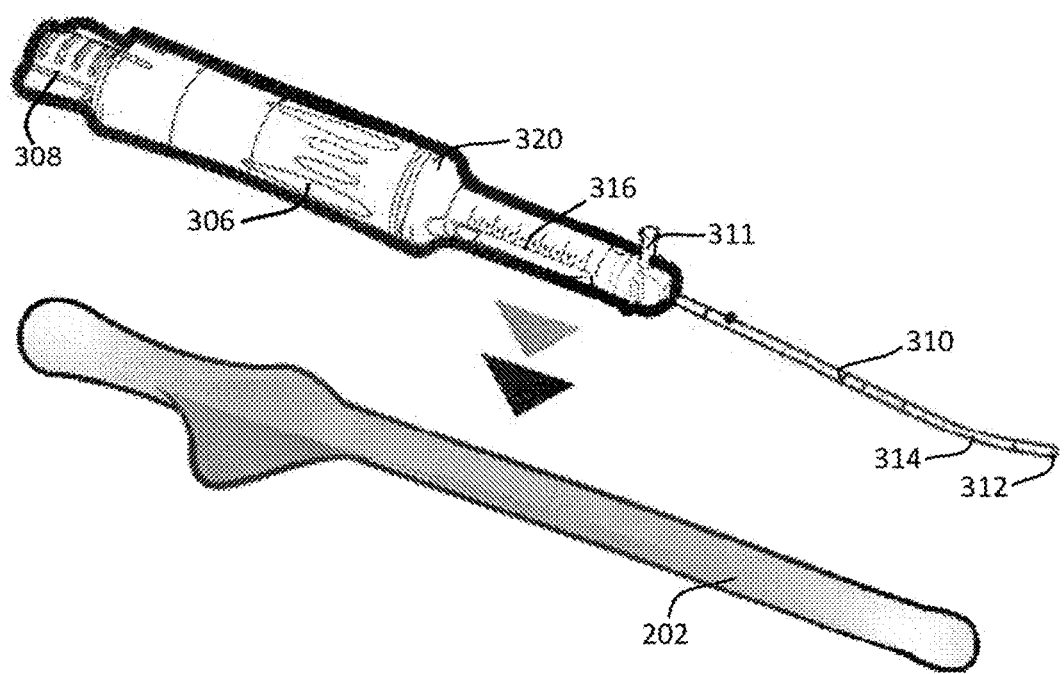
FIG. 3 illustrates an exemplary coupling of the ultrasound transducer and the device for ablation of uterine fibroids, in accordance with an embodiment of the present disclosure.

FIG. 3 illustrates an exemplary coupling of the ultrasound transducer and the device for ablation of uterine fibroids, in accordance with an embodiment of the present disclosure. In one embodiment, the device 204 and the ultrasound transducer 202 can be used separately, as described earlier. The ultrasound transducer 202 is used to provide a volume scan of the uterus, while the device 204 can be navigated such that it can be positioned near a fibroid on the uterus. The electrode 200 is provided within the sheath 208, which can be exposed when the electrode 200 is pushed out of the sheath 208, which, when supplied with power, ablates the fibroid.

Once a sufficient number of volume scan data are received by the planning works station 500, the location other parameters of the fibroid such as, but not limited to overall volumes of each fibroid, the location of the fibroids within the uterus, the location of the fibroid 706 with reference to the wall of the uterus 704 are determined by the dedicated software based on the images recorded at the planning works station. The parameters are determined based on image auto or manual segmentation and contour recognition. Though these are generally known in the art, the disclosed system 100 comprises the software with special features so that the results make it easier for the gynaecologist to perform the ablation. Based on the frames automatically or manually segmented from the volume scan data, a 3D rendered uterus model can be generated.

Based on these rendered 3D model, the planning workstation 500 provides recommendations of the sequence in which the fibroids 706 are to be ablated in case there are more than one fibroid. The planning workstation 500 also provides the ablation parameters for each of the fibroids 706. The ablation parameters may be one or more of a power and duration of the ablation. The planning workstation 500 also recommends the positioning of the device 204 such that RF electrode 200 can precisely reach out to exact location of fibroid(s) 706. The electrode 200 is exposed when pushed out through the sheath to expose a required length of the distal end of the RF electrode with the help of a control means.

In certain embodiment, however the gynaecologist/surgeon may overrule the recommendations of the planning workstation and choose own parameters for the ablation process.

The RF electrode 200 is inserted into the uterus through the cervical canal. It is to be noted here that there may not be any piercing, or any other invasive process involved in this. However, it is possible that for certain fibroids that are located within the wall of the uterus 704 (referred to as intra mural in relevant literature) it may be necessary to pierce through the covering tissue. Also, there is a possibility that because of the location of the fibroid the shortest and the most appropriate path for the RF electrode to reach it is by piercing the uterine wall itself. In either of the cases, there is no need for dilation of the cervix. This is done under the visual guidance provided by the images on the planning workstation 500 which also provides real time or near real time images of the RF electrode 200 in the uterus. This visual guidance may be in the form of an overlaid electrode tracking line on the displayed image, the overlay being an inventive feature of the software of the system of the present disclosure.

Further, by manoeuvring the RF electrode 200, the active length of the electrode in particular of the tubular structure 208 is placed on the fibroid 706 for optimum results.

In the next step, the ablation parameters, namely power and duration, are set on the RF source 300 and the RF source is turned on for delivering the set RF power to the RF electrode 200. This heats the fibroid being ablated and that ablation continues till the set time is elapsed. During this whole time the ultrasound scanner 600 continues its scanning and communicates the images to the planning workstation 500.

The system 100 of the present disclosure has a feature for depicting the ablation volume graphically with respect to the fibroid(s) 706. In one embodiment, the planning workstation may provide a visual or auditory warning to the gynaecologist, or both.

As described above the process of positioning, ablating, guiding, recommendations are repeated for each of the fibroids until all the fibroids that were planned to be ablated. It is to be noted that it may not be necessary to ablate all the fibroids present in the uterus of a patient. It is possible that depending on the type of the fibroid or its structure or its consistency, as visible to in the ultrasound images precludes the need for ablating them. In other words, only those fibroids that are deemed to be symptomatic are chosen to or planned to be ablated. It is also possible that a fibroid is too small to be ablated without damaging the tissue proximate or surrounding it, and so on.

Thus, the present disclosure provides the system that is cost effective, minimally invasive, safe and clinically effective system to treat uterine fibroids.

The system in accordance with the present disclosure, is the system the operation of which does not require specialized skills and can be acquired by gynaecologists/surgeons to carry out ablation of uterine fibroid to deliver the treatment, with a reasonable amount of training.

In another aspect, the present disclosure provides a device for carrying out ablation of uterine fibroid(s), said device comprising: a sheath provided at an end of the device, said end being in a direction of insertion of the device into the uterine cavity, said sheath covering an electrode provided on the device that is configured for ablation of uterine fibroid(s); an angle provided towards a distal end of the sheath, wherein the angle enables the end of the sheath to reach walls of the uterine cavity, and wherein the angle affords support to the electrode; markings provided on the sheath to enable determination of extent of insertion of the device into the uterine cavity; rotary markings provided on the device to enable determination of rotational orientation of the sheath; and a rotary mechanism provided in the carriage barrel assembly such that rotation applied to the mechanism causes a linear motion of the electrode outwards from the sheath to enable the electrode to pierce the uterine fibroid(s).

In an embodiment, the device is provided with electrode markings to determine extent of extension of the electrode.

In another embodiment, the device is provided with orientation markings to enable determination of the orientation of the angle of the sheath within the uterine cavity with respect to the device.

In another embodiment, the device is provided with an actuator configured to initiate outward extension of the electrode. It can be appreciated that the RF electrode can be any electrode available in the art.

In another embodiment, the device is coupled to a RF source such that, on receipt of an instruction, the RF source is configured to provide RF power to the electrode to enable ablation of the fibroid(s).

FIGS. 4A-4D illustrate exemplary views of a device for ablation of uterine fibroids that is capable of providing navigational cues to a user of the device for positioning the device at a required location for performing ablation operation, in accordance with an embodiment of the present disclosure.

In an embodiment, the device can comprise a carriage barrel assembly 408; a sheath 404; and a housing 406.

Figure 4A:
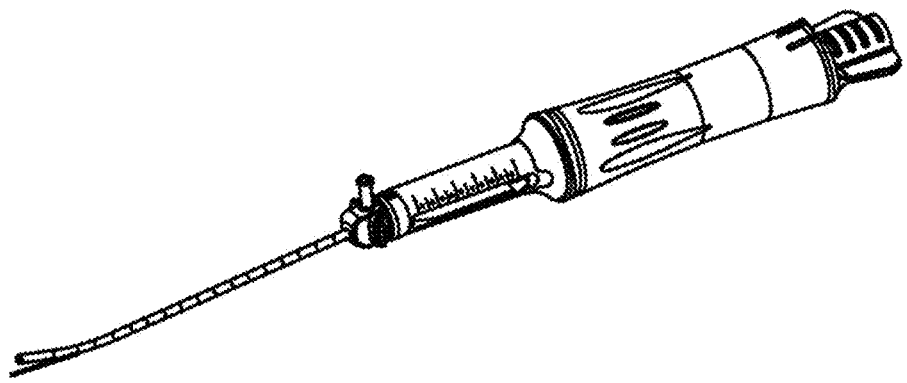
FIGS. 4A-4D illustrate exemplary views of a device for ablation of uterine fibroids that is capable of providing navigational cues to a user of the device for positioning the device at a required location for performing ablation operation, in accordance with an embodiment of the present disclosure.
Figure 4B:
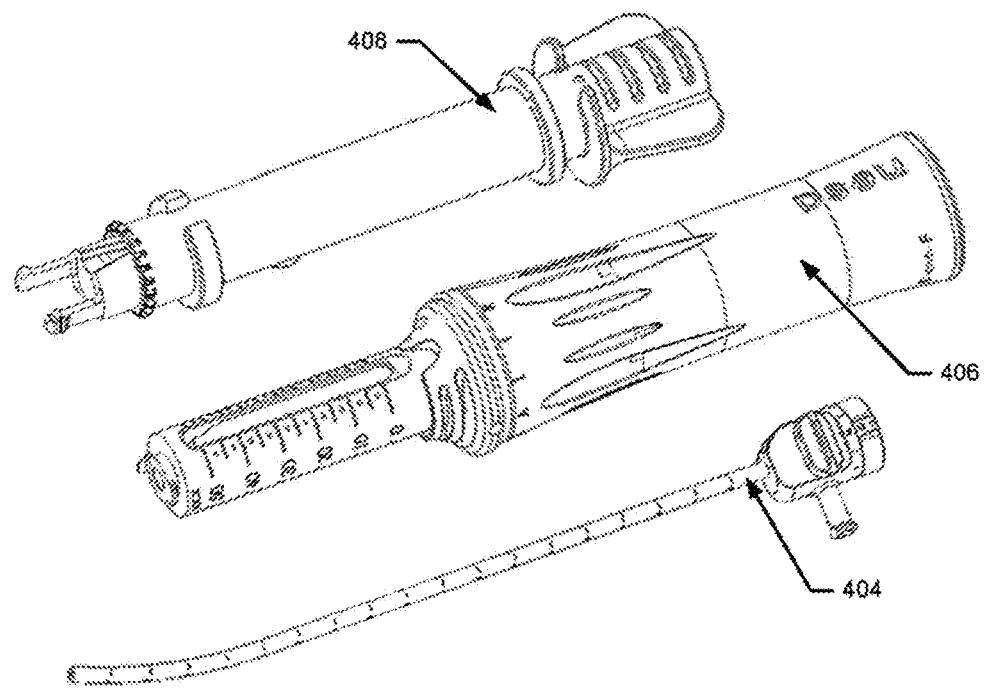
Figure 4C:
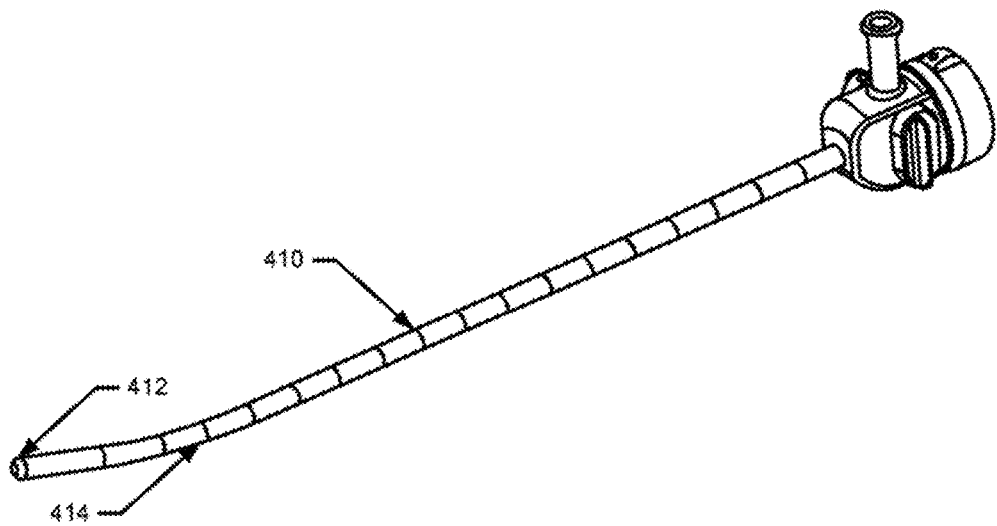

Referring to FIG. 4C, the sheath 404 comprises sheath markings 410 along length of the sheath; a rounded tip 412 at a distal end of the sheath; and a sheath angle 414 provided near the distal end of the sheath.

The markings 410 provide feedback to the user of the device on how much of the sheath of the device is inserted in the uterine cavity. In an exemplary embodiment, the markings can be spaced about 5 mm apart.

The sheath, near the end, is provided with an angle, so provided as to easily reach the walls of the uterine cavity. Further, the angle provides support to the electrode provided within the sheath as the electrode penetrates the fibroid. The angle can be measured based on a relationship between a curved length of the sheath and the depth of the sheath. In an embodiment, curved length-depth can be any of 50-10, 55-10 and 55-15, thereby forming an angle in the range of 15 degrees to 24 degrees. In an exemplary embodiment, the preferable curved length-depth can be 55-10 translating to an angle of about 15 degrees. The round tip of the sheath allows the sheath to advance within the uterine cavity without harming or infiltrating any surrounding tissue.

In another embodiment, the device can be provided with orientation markings such that the orientation of the sheath in a circular plane can be gauged such that the sheath is guided to the appropriate point of interest in the uterus and in the correct orientation for the electrode to come out and pierce the fibroid. The orientation markings can be provided as a angle of rotation markings. In one exemplary embodiment, there are 12 orientation markings such as in a clock.

In another embodiment, the sheath can be coupled to the housing, the coupling provided with a rotate and lock feature. The locking mechanism can be such that the sheath can be assembled to the housing in one orientation, i.e., with the angle of the sheath being at the distal end of the housing. This provides a poka-yoke feature to the coupling of the sheath to the housing. This is done in order that the markings on the sheath provide a feedback to the user on the exact position of the bent direction of the sheath. In another embodiment, the sheath can have a male luer connector where a tubing can be attached to provide a flushing liquid.

In another embodiment, the marking on the sheath and the housing are so aligned that the sheath can be used with other devices as well and can provide accurate feedback to the user on the orientation and position of the device within the uterine cavity.

Figure 4D:
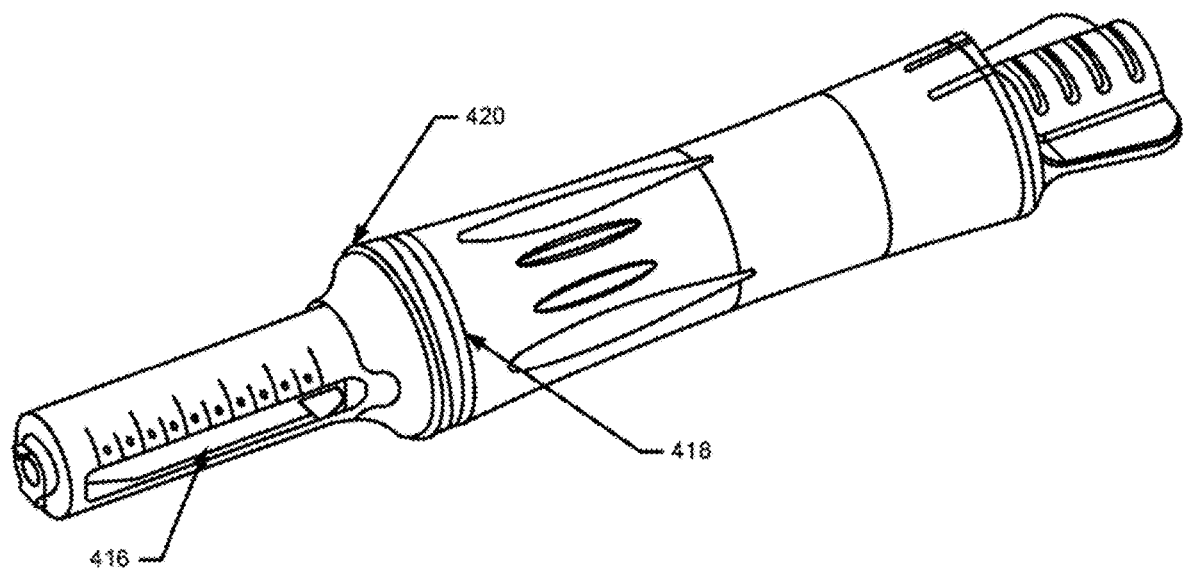

Referring to FIG. 4D, the device can be provided with a marking to measure movement of electrode 416; an orientation marking 418; and an actuator switch 420. The orientation marking can allow the user to gauge the orientation of the sheath within the uterine cavity with respect to the device.

In another embodiment, the device is configured such that a rotational force provided at the carriage barrel of the device can translate into a linear motion of the electrode and the force is transferred uniformly by the pin movement along a desired path. The marking can provide feedback on the incremental advancement of the electrode.

In another embodiment, the rotational design of the device includes a cam follower mechanism with a pitch of about 55 mm. Studies have determined that the penetration force required for the electrode to pierce the fibroid is about 20 N. The device of the present disclosure is configured to provide a penetration force of at least more than 20 N. In an exemplary embodiment, the device is configured to provide a penetration force in the range of 20 N to 38 N.

In another embodiment, the device can be provided with an actuator to enhance the safety of the device. The actuator controls the movement of the electrode and this can prevent adverse situations due to unnecessary movement of the electrode.

In another embodiment, the diameter of the sheath is about 4-5 mm. This allows the sheath to be inserted into the cervix of a patient without much cervical dilation, and this means that minimal local sedation is required. This makes the use of the device safer for the patient.

In certain embodiments, the present disclosure provides a method for ablation of uterine fibroid(s). The method for ablation of uterine fibroid(s) comprises:
  a) inserting an ultrasound transducer through the vagina of the patient until distal end of said transducer meets the cervix and carrying out a trans-vaginal volume scan by positioning the transducer in two orientations orthogonal to each other;
  b) identifying the fibroid(s) to be ablated based on 3D rendered model presented by the planning workstation, wherein the 3D rendered uterus model is created based on the ultrasound images obtained from processing the volume scan and also the frames which are auto segmented/manually segmented;
  c) computing navigation ablation parameters for ablation of each of fibroid selected from the 3D rendered uterus model, based on the images by the dedicated software preloaded on to the planning workstation. Here the navigation parameters can include, but not be limited to the length of insertion of the sheath in order that the sheath is positioned close to the fibroid, orientation of the device required such that the sheath is positioned with respect to a required point in the fibroid and the length of electrode required to be pushed from the sheath to reach the required point in the fibroid;
  d) computing a graphical representation of ablation volume based on the volume of the fibroid, the presence or absence of other organs and sensitive tissues proximate to the fibroid and the distance between the fibroid and the organs and sensitive tissues;
  e) arriving at the ablation parameters selected from a power for ablation, duration of ablation;
  f) placing the active length of the RF electrode proximate to the fibroid to be ablated based on the determined parameters for ablation of fibroid by controlling the RF electrode with controls provided on the navigation system of the RF electrode;
  g) initiating the ablation by instructing the RF source to deliver the RF power to the RF electrode with the help of a means for providing such command to the RF source;
  h) terminating the ablation in either or both the event(s) of exceeding the pre-set duration or any suspension of ablation spreading beyond the unintended region for allowing the ablation to exceed in the sensitive regions;
  i) in an event of completion of the ablation of the fibroid, the RF electrode is retracted; and
  j) optionally repeating the steps (a) to (j) for ablating next fibroid or fibroids as per the pre-determined order of ablation in said method the sequence of one or more steps may be altered suitably by the planning workstation or an input provider.

In an embodiment, the means for providing the command to the RF source selected from a push button or a foot pedal is pressed to provide the command to the RF source to deliver the RF power to the RF electrode for initiating the ablation.

When all the fibroids identified are ablated, a suitable input is provided by the gynaecologist or surgeon to the planning workstation and method is terminated.

It is to be noted that certain sequence of steps may be altered, in some implementations, advantageously by a person skilled in the art and all such variations fall within the scope of this disclosure.

It is also possible that some of the steps may be automated for example, segmenting of fibroid(s) and uterus, the setting of the power and duration of ablation of a fibroid may be set automatically by the planning work station, in a known way, and all such variations, additions or improvements of features fall under the scope of this disclosure.

In an embodiment, the workflow of planning workstation can be elucidated in the form of various modules encompassing set of activities.

In an embodiment, the present disclosure can provide an exemplary module diagram for the proposed system for ablation of uterine fibroids, in accordance with an embodiment of the present disclosure. In an embodiment, the system can include an ultrasound scanner as available in the art. The ultrasound scanner can be coupled with the planning workstation in order to facilitate the device of the present disclosure to ablate uterine fibroid(s).

In another embodiment, the planning workstation can comprise processors configured for functions such as,
  Processing ultrasound images to extract a three-dimensional graphical representation of the uterus.
  Extracting fibroid locations in the uterus.
  Computing navigation parameters for the device such that the sheath and the electrode can enter and position themselves in an appropriate location for ablation of the fibroid.
  Determining the ablation parameters for ablation of the fibroid.
  Recommend a sequence for ablation of multiple fibroids, if present.

Figure 5:
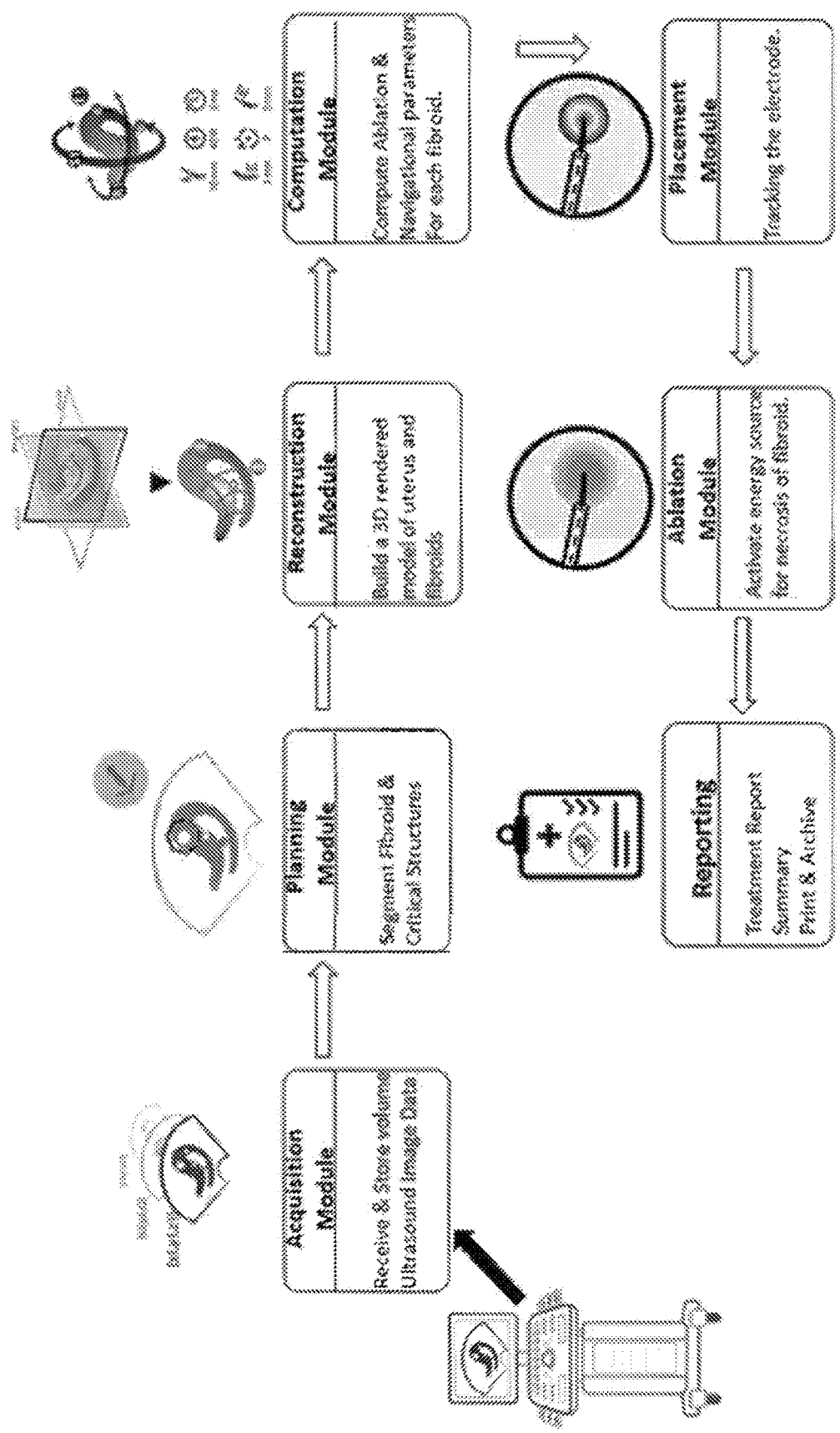
FIG. 5 illustrates an exemplary workflow of the planning workstation in terms of different modules and activities covered by said modules, in accordance with an embodiment of the present disclosure.

FIG. 5 illustrates an exemplary workflow of the planning workstation in terms of different modules and activities covered by said modules, in accordance with an embodiment of the present disclosure. Referring to FIG. 5 the workflow of the planning workstation comprises:
  a) an acquisition module for recording the volume scan images, and providing feedback on the scan coverage;
  b) a planning module for marking either manually or auto-segmented fibroid and critical structures like sensitive regions or organs around fibroid to be ablated, carry out measurements and arrive at a plan to for ablation of uterine fibroid(s) for desired clinical outcome and effective treatment of patient;

c) a reconstruction module for building a 3D rendered model of uterus from processing of volume scan images;

d) a computational module for calculating the navigational and ablation parameters for each of the fibroid, also for exhibiting guidance graphics to determine correct placement of electrode;

e) a placement module for tracking the RF electrode to the exact location of the fibroid;

f) an ablation module for computing navigation parameters and ablation parameters for the device; and g) a reporting module for compiling report, editing, commenting, follow-up data printing and archiving.

The workflow of the planning workstation defined in the form of different modules provides much ease to comprehend activities covered at various stages of the method as per the present disclosure.

The method for the ablation of uterine fibroids in accordance with the present disclosure is described hereunder in detailed manner, with reference to FIG. 5. For the sake of clarity, the steps performed by a human being, in this case a gynaecologist or a surgeon treating a patient with uterine fibroids, are shown in dotted line blocks and the others performed by the planning workstation or a digital computer per se, are shown in solid lines. The difference is also set out in the description that follows.

Figure 6:
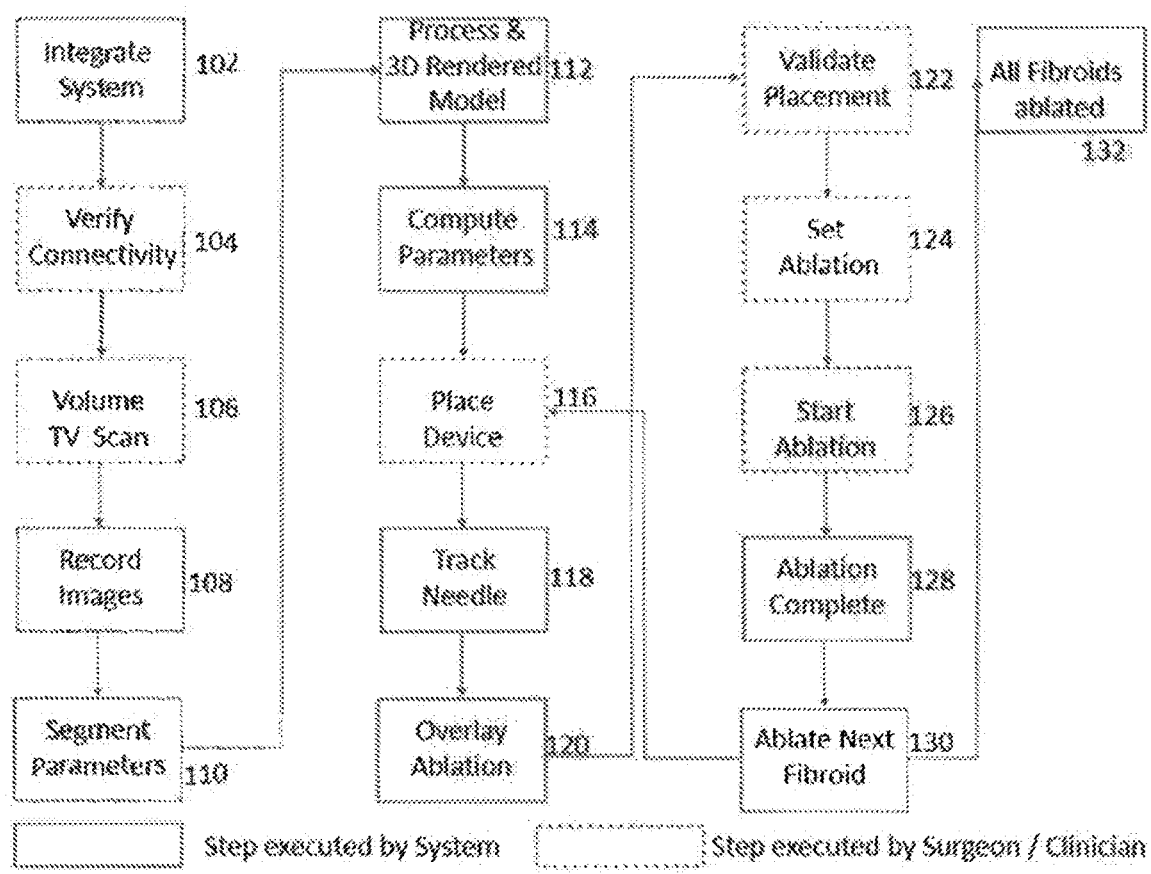
FIG. 6 in conjunction with FIGS. 1-5, sets forth, in detail, the method for ablating uterine fibroid(s).

FIG. 6 in conjunction with FIGS. 1-5, sets forth in detail the method for ablating uterine fibroid(s).

In an optional step 102, for constructing a system in accordance with the present disclosure, a trans-vaginal ultrasound transducer 202 is functionally connected to an ultrasound scanner 600. RF electrode 200 is integrated with a navigation system. The ultrasound scanner 600 is functionally connected to the planning workstation 500. If the ultrasound scanner is used for other purposes, this step is performed every time the ultrasound scanner is used for the ablation of uterine fibroids. Otherwise, the setting up step is not needed and the system with requisite components, and assembly is in a ready to use state.

In step 104, connectivity between the components of the system, namely, the ultrasound transducer 202, ultrasound scanner 600, the planning system 500. The device 204 and the RF electrode 208 is verified.

In step 106, the ultrasound transducer 202 is inserted through the vagina of the patient until its distal end meets the cervix. The trans-vaginal ultrasound volume scan is performed with the ultrasound transducer 202 by sweeping the probe in two orientations orthogonally. Entire volume scan images are recorded in planning system 500 in a known way.

In step 108, the ultrasound images are recorded at the planning system 500.

In steps 110-114, the ultrasound volume images obtained from the two orthogonal orientations of the ultrasound transducer are converted into three dimensional (3D) rendered uterus model by the planning workstation 500. The fibroids 706 are identified and the parameters for location of each of them are calculated based on the images by the dedicated software preloaded on to the planning workstation. The planning workstation also detects the sensitive regions around the fibroid for presentation to the gynaecologist or surgeon. The planning workstation also computed navigational and ablation parameters for each of the fibroids.

The planning workstation presents the 3D rendered uterus model to the gynaecologist or surgeon to enter the inputs about the fibroids to be ablated. The planning workstation 500 then recommends the order of the ablation of the selected fibroids. Based on clinical expertise, the gynaecologist or surgeon may change the order presented by the planning workstation. This is input into the planning workstation by the gynaecologist or surgeon. The planning workstation 500 receives this information for further processing.

A safe ablation volume is determined by the planning workstation based on the volume of the fibroid, the presence or absence of other organs and sensitive tissues proximate to the fibroid and the distance between the fibroid and the organs and sensitive tissues. The planning workstation presents this information to the gynaecologist or surgeon, which can be changed by the gynaecologist or surgeon. The gynaecologist or surgeon inputs the selection information into the planning workstation. The planning workstation based on the received input calculates the ablation parameters such as the power for ablation, the duration of ablation, and the active length of the RF electrode 200. This is done based on a Numerical model or extrapolation of values from experimental tests. The planning workstation presents these parameters to the gynaecologist or surgeon for acceptance or modification. It can be appreciated here that methods other than numerical model or extrapolation of values can be employed for determination of ablation parameters.

In step 116, the controls on the navigation system are used by gynaecologist or surgeon to place the active length of the RF electrode 208 based on the suggestion by planning system 500.

In step 118, after placing the RF electrode, the planning workstation tracks the RF electrode movement 200 has been placed as needed. In step 122 the planning workstation validates 500 if the RF electrode has been placed correctly as per the recommendations in step 114, using the ultrasound images received from the ultrasound scanner 600.

In step 120, the ablation parameters are set in the RF generator either manually by the gynaecologist or automatically by the planning workstation.

In steps 124, and 126, ablation is initiated by instructing the RF source 300 to deliver the RF power to the RF electrode 200 for example by a push button or pressing a foot pedal 400 of the RF source provided for the purpose.

In step 128, upon ablation of all the selected fibroids, the RF electrode is retracted to avoid any scrapping of endometrium or tissues.

In step 130, the next fibroid for ablation is selected. All the relevant steps, for instance steps 108 to 128 are repeated, until all the fibroids selected by the gynaecologist are ablated.

In step 132, the method is terminated when all the identified fibroids are ablated and when a gynaecologist or surgeon provides the input to the planning workstation.

It is to be noted that certain sequence of steps may be altered, in some implementations, advantageously by a person skilled in the art and all such variations fall within the scope of this disclosure. It is also possible that some of the steps may be automated by a person skilled in the art. For example, the setting of the power and duration of ablation of a fibroid may be set automatically by the planning workstation on the RF source by establishing communication between the two, in a known way, and all such variations, additions or improvements of features fall under the scope of this disclosure.

Advantages

The present disclosure provides a cost effective, minimally invasive, safe, cost efficient, and clinically effective system and method to treat uterine fibroids.

The system comprises integrating with ultrasound machine of any make normally available at a gynaecologist clinic or hospital.

The system that can be used to treat uterine fibroids outside of an operating theatre or can be delivered and operated in a limited resource setting of the gynaecologist's office commonly referred to as a minor operation theatre or in-office.

The use of such a system does not need highly skilled gynaecologists. The operation of the system to carry out ablation of uterine fibroids does not require specialized skills and can be acquired by gynaecologists, with a reasonable amount of training.

From the foregoing, it will be appreciated that, although specific embodiments of the invention have been described herein merely for purposes of illustration, various modifications may be made without deviating from the spirit and scope of the invention and should not be construed so as to limit the scope of the invention or the appended claims in any way.

We claim:

1. A system for ablation of uterine fibroid(s), said system comprising:
    an ultrasound scanner configured to perform a volume scan of a uterus of a patient;
    a display coupled with the ultrasound scanner, configured for displaying image and alphanumeric characters;
    a device comprising a sheath and an electrode, the sheath covering the electrode, the electrode being configured for ablating the uterine fibroid, wherein the sheath is provided at an end of the device, the end being in a direction of insertion of the device into the uterine cavity;
    a controllable energy source coupled with the electrode and configured to supply energy to the electrode;
    one or more processors operatively coupled with a memory, said memory storing instructions executable by the one or more processors to:
        receive ultrasound image data from the ultrasound scanner;
        process the ultrasound image data to generate a three-dimensional representation of the uterus of the patient;
        determine location and size of one or more fibroids in the uterus;
        determine one or more navigation parameters for the electrode, from the display;
        determine ablation parameters required by the electrode to ablate the fibroid,
    wherein the device is operatively coupled to the one or more processors, said one or more processors configured to guide the electrode to a required point in the fibroid based on the determined one or more navigation parameters on the display, and
    wherein, on receipt of a signal, the controllable energy source supplies power to the electrode to enable ablation of the fibroid, wherein the processing of the ultrasound image data occurs on a planning workstation, and wherein the planning workstation is configured to, based on the processed ultrasound image data, compute the one or more navigation parameters selected from a group comprising the length of insertion of the sheath in order that the sheath is positioned close to the fibroid, orientation of the device required such that the sheath is positioned with respect to a required point in the fibroid, the length of the electrode required to be pushed from the sheath to reach the required point in the fibroid, and a combination thereof.

2. The system as claimed in claim 1, wherein a transducer is introduced through a vagina of the patient for carrying out a trans-vaginal scan of the uterus.

3. The system as claimed in claim 1, wherein the device is introduced through a vagina of the patient and is further guided into the uterus through a cervix.

4. The system as claimed in claim 1, wherein the controllable energy source is selected from a group comprising a radiofrequency (RF) source, a microwave source, a laser source and a cryo source.

5. The system as claimed in claim 1, wherein the controllable energy source is configured to set the ablation parameters for the ablation of the fibroid, and to set the duration of the ablation process.

6. The system as claimed in claim 1, where in the device for carrying out ablation of the uterine fibroid(s) comprises:
    an angle provided towards a distal end of the sheath, wherein the angle enables the end of the sheath to reach the one or more fibroids in the uterus;
    markings provided on the sheath to enable determination of extent of insertion of the device into the uterine cavity;
    rotary markings provided on the device to enable determination of rotational orientation of the sheath; and
    a carriage barrel assembly that translates rotational force to a linear motion of the electrode outwards from the sheath to enable the electrode to pierce the uterine fibroid(s).

7. The system as claimed in claim 1, wherein the planning workstation, based on the processed ultrasound image data, is configured to determine the ablation parameters from the location and size of the fibroid from a database operatively coupled to the planning workstation, said database containing a dataset of corresponding parameters for ablation of a plurality of fibroids.

8. The system as claimed in claim 7, wherein, based on the ablation parameters of a selected uterine fibroid, a safe volume for ablation of the fibroid is computed and represented graphically, based on presence of tissues in the vicinity of the fibroid that are not meant to be ablated.

9. The system as claimed in claim 1, wherein the planning workstation provides real time guidance and tracking while the electrode is being positioned at the required point in the fibroid.

10. A device for carrying out ablation of uterine fibroid(s), said device comprising:
    a sheath provided at an end of the device, said end being in a direction of insertion of the device into the uterine cavity, said sheath covering an electrode provided on the device that is configured for ablation of the uterine fibroid(s);
    an angle provided towards a distal end of the sheath, wherein the angle enables the end of the sheath to reach walls of the uterine cavity, and wherein the angle affords support to the electrode;
    markings provided on the sheath to enable determination of extent of insertion of the device into the uterine cavity;
    rotary markings provided on the device to enable determination of rotational orientation of the sheath; and
    carriage barrel assembly that translates rotational force to a linear motion of the electrode outwards from the sheath to enable the electrode to pierce the uterine fibroid(s).

11. The device as claimed in claim 10, wherein the angle provided is not more than 24 degrees and is in the range of 15 degrees to 24 degrees.

12. The device as claimed in claim 11, wherein the angle provided is 15 degrees.

13. The device as claimed in claim 10, wherein the translation of the rotational force to the linear motion enables generation of force not less than 20 N, and in the range of 20 N and 38 N to enable the electrode to pierce the uterine fibroid(s).

14. The device as claimed in claim 10, wherein the device is provided with sheath markings on the sheath to determine extent of insertion of the sheath into the uterus, the sheath markings preferably being separated by 5 mm.

15. The device as claimed in claim 10, wherein the device is provided with electrode markings to determine extent of extension of the electrode, the electrode markings preferably being separated by 2.5 mm.

16. The device as claimed in claim 10, wherein the device is provided with orientation markings to enable determination of the orientation of the angle of the sheath within the uterine cavity.

17. The device as claimed in claim 10, wherein the device is provided with an actuator configured to initiate outward extension of the electrode.

18. The device as claimed in claim 10, wherein the device is configured to be operated by any or a combination of manual means, electronic means and a combination thereof based on navigation parameters displayed on a visual display operatively coupled to the device, to enable the device to be guided to a required point for ablation of the uterine fibroid.

19. The device as claimed in claim 10, wherein the device is coupled to an energy source such that, on receipt of an instruction, the energy source is configured to provide ablation parameters and energy to the electrode to enable ablation of the fibroid(s).

20. A method for ablation of uterine fibroid(s), the method comprising the steps of:
- performing, using an ultrasound scanner, a volume scan of a uterus of a patient;
- receiving, at a computing device, ultrasound image data from the ultrasound scanner, said ultrasound image data being displayed on a display configured for image and alphanumeric characters;
- processing, at the computing device, the ultrasound image data to generate a three-dimensional representation of the uterus of the patient;
- determining, at the computing device, location and size of one or more fibroids in the uterus;
- determining, at the computing device, one or more navigation parameters for guiding a device comprising a sheath and an electrode, the sheath covering the electrode, the electrode being configured for ablating the uterine fibroid, wherein the sheath is provided at an end of the device, the end being in a direction of insertion of the device into the uterine cavity, at a required point in the fibroid in the uterus;
- determining, at the computing device, ablation parameters required by the electrode to ablate the fibroid;
- guiding, using one or more navigation parameters computed by a computing device, the device to enable the electrode to be positioned at the required point in the fibroid,
- wherein, on receipt of a signal, the controllable energy source supplies power to electrode to enable ablation of the fibroid, wherein the processing of the ultrasound image data occurs on a planning workstation, wherein, based on the processed ultrasound image data, the one or more navigation parameters are computed, via the planning workstation, and wherein the one or more navigation parameters are selected from a group comprising the length of insertion of the sheath in order that the sheath is positioned close to the fibroid, orientation of the device required such that the sheath is positioned with respect to a required point in the fibroid, the length of electrode required to be pushed from the sheath to reach the required point in the fibroid, and a combination thereof.

21. The method as claimed in claim 20, wherein a transducer is introduced through a vagina of the patient for carrying out a trans-vaginal scan of a uterus.

22. The method as claimed in claim 20, wherein the device is introduced through a vagina of the patient and is further guided into the uterus through a cervix.

23. The method as claimed in claim 20, wherein the controllable energy source is selected from a group comprising a radiofrequency (RF) source, a microwave source, a laser source and a cryo source.

24. The method as claimed in claim 20, wherein the controllable energy source is configured to set the ablation parameters for the ablation of the fibroid, and to set the duration of the ablation process.

25. The method as claimed in claim 20, wherein the planning workstation, based on the processed ultrasound image data, is configured to determine the ablation parameters from the location and size of the fibroid from a database operatively coupled to the planning workstation, said database containing a dataset of corresponding parameters for ablation of a plurality of fibroids.

26. The method as claimed in claim 25, wherein, based on the ablation parameters of a selected uterine fibroid, a safe volume for ablation of the fibroid is computed and represented graphically, based on presence of tissues in the vicinity of the fibroid that are not meant to be ablated.

27. The method as claimed in claim 20, wherein the planning workstation provides real time guidance and tracking while the electrode is being positioned at the required point in the fibroid.

* * * * *